United States Patent

King et al.

[11] Patent Number: 5,859,040
[45] Date of Patent: Jan. 12, 1999

[54] SYNERGISTIC ANTIMICROBIAL COMPOSITIONS CONTAINING 1-HYDROXYMETHYLPYRAZOLE AND A PRESERVATIVE

[75] Inventors: Vanja M. King; Xiangdong Zhou, both of Memphis, Tenn.

[73] Assignee: Buckman Laboratories International, Inc., Memphis, Tenn.

[21] Appl. No.: 863,691

[22] Filed: May 27, 1997

Related U.S. Application Data

[62] Division of Ser. No. 580,739, Dec. 29, 1995, Pat. No. 5,661,149.

[51] Int. Cl.$^6$ .......................... A01N 33/18; A01N 43/50; A01N 43/56

[52] U.S. Cl. .......................... 514/389; 514/406; 514/407; 514/727

[58] Field of Search .................................. 514/406, 407, 514/727, 389

[56] References Cited

U.S. PATENT DOCUMENTS

| | | | |
|---|---|---|---|
| 3,865,724 | 2/1975 | Shema et al. | 210/62 |
| 4,801,362 | 1/1989 | Fenyes | 252/51 |
| 4,844,891 | 7/1989 | Rosen et al. | 424/76.4 |
| 5,041,457 | 8/1991 | Hsu | 514/372 |
| 5,198,440 | 3/1993 | Oppong et al. | 514/241 |
| 5,225,432 | 7/1993 | Fenyes et al. | 514/407 |
| 5,278,178 | 1/1994 | Hsu | 514/372 |
| 5,441,979 | 8/1995 | Oppong et al. | 514/515 |
| 5,441,981 | 8/1995 | Oppong et al. | 514/544 |

FOREIGN PATENT DOCUMENTS

| | | |
|---|---|---|
| 0 467 708 A | 1/1992 | European Pat. Off. . |
| 0 484 172 A1 | 5/1992 | European Pat. Off. . |

OTHER PUBLICATIONS

Buckman Laboratories Formulation Sheet No. L27W (Jan. 1994), "Hair Conditioner with Busan® 1504," ©1993.
Buckman Laboratories Formulation Sheet No. L26W (Jan. 1994), "Protein Shampoo with Busan® 1504," ©1993.
Buckman Laboratories Solubility Data Sheet No. L25W (Jan. 1994), "Solubility of Busan® 1504 in Common Cosmetic Ingredients," ©1993.
Buckman Laboratories Efficacy Profile Sheet No. L17W (Jul. 1993), "Busan® 1504 Efficacy in a Hair Conditioner USP XXII Challenge Test Method," ©1993.
Buckman Laboratories Efficacy Profile Sheet No. L16W (Jul. 1993), "Busan® 1504 Efficacy in a Protein Shampoo USP XXII Challenge Test Method," ©1993.
Buckman Laboratories Product Profile Sheet No. L5W (Jun. 1992),"Busan®1504" ©1992.
Buckman Laboratories Product Profile Sheet No. L6W (Jun. 1992), Busan® 1506 ©1992.
Buckman Laboratories Analytical Method Sheet No. L11W (Mar. 1993), "Busan® 1504" ®1993.

*Primary Examiner*—Allen J. Robinson
*Attorney, Agent, or Firm*—Armstrong, Westerman, Hattori, McLeland & Naughton

[57] ABSTRACT

Compositions comprising a compound of formula I

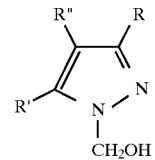

where R and R' are independently selected from hydrogen and alkyl of 1 to 4 carbon atoms, R" is a moiety selected from the group consisting of (a) hydrogen, (b) a halogen atom selected from the group consisting of F, Cl, Br, and I, and (c) a nitro group, or the hydrochloride salt of said compound; and at least one preservative are disclosed which are synergistically effective compared to the respective components alone in controlling and/or reducing the growth of microorganisms in or on a material or medium. Methods to control and/or reduce the growth of microorganisms and prevent spoilage caused by microorganisms with the use of the compositions of the present invention are also disclosed.

26 Claims, No Drawings

SYNERGISTIC ANTIMICROBIAL COMPOSITIONS CONTAINING 1-HYDROXYMETHYLPYRAZOLE AND A PRESERVATIVE

This is a divisional of application Ser. No. 08/580,739 filed Dec. 29, 1995 now U.S. Pat. No. 5,661,149.

The present invention relates to certain compositions and processes useful for controlling the growth of one or more microorganisms and for preventing spoilage caused by bacteria and/or fungi in various products, materials, or media, particularly industrial products, materials or media. These materials or media include for example, wood pulp, wood chips, lumber, adhesives, coatings, animal hides including birds and reptiles, paper mill liquors, paper, optical brighteners, pharmaceutical and chemical formulations, cosmetics and toiletry formulations, geological drilling lubricants and aids, agrochemical compositions, paints, leathers, wood, metalworking fluids, industrial process aid formulations, cooling tower water, waste water, pasteurizers, tanning liquors, starch, dyes, petrochemicals, surfactants, defoamers, emulsions or water containing polymers, lipid based materials, carbohydrate based materials, proteinaceous materials, acrylic latex paint emulsions, and textiles. The novel processes and mixtures of the present invention show unexpected synergistic activity against microorganisms, including bacteria and fungi. Specifically, the invention is directed to the use of compositions comprising dimethylhydroxymethylpyrazole and at least one preservative.

Many of the products, materials, or media referred to above, when wet, subjected to treatment in water, or placed in a humid environment, are susceptible to bacterial and/or fungal deterioration or degradation unless steps are taken to control such degradation or deterioration.

To control deterioration or degradation caused by microorganisms, various microbicides are used. Workers in the trade have continued to seek improved biocides that have low toxicity and are capable of exhibiting a prolonged biocidal effect at normal use levels.

Preservatives can be used alone to control microorganisms, but many of them have low efficacy against bacteria and fungi unless extremely high concentrations are used. 1-hydroxymethylpyrazoles can also be used alone in low concentrations as a biocide.

This invention provides a microbicidal composition capable of controlling the growth of at least one microorganism, particularly fungi and bacteria, over prolonged periods of time. Additionally, the present invention provides compositions which are economical to use. Methods of controlling the growth of at least one microorganism are also objects of this invention.

The present invention provides a composition comprising a 1-hydroxymethylpyrazole and at least one preservative, where the components are present in a combined amount synergistically effective to control the growth of at least one microorganism.

The present invention also provides a method for controlling the growth of at least one microorganism in or on a material or medium susceptible to attack by the microorganism. That method comprises the step of adding to the material or medium a composition of the present invention in an amount synergistically effective to control the growth of the microorganism.

The present invention also embodies the separate addition of a 1-hydroxymethylpyrazole and at least one preservative to the products, materials or media described above. According to this embodiment, the components are individually added to the system so that the final amount of the 1-hydroxymethylpyrazole and at least one preservative present in the system at the time of use is that amount synergistically effective to control the growth of at least one microorganism.

The compositions of the present invention are also useful in preserving various types of industrial media or materials susceptible to attack by microorganisms. Such media or materials include, but are not limited to, wood pulp, wood chips, lumber, adhesives, coatings, animal hides including birds and reptiles, paper mill liquors, paper, optical brighteners, pharmaceutical and chemical formulations, cosmetics and toiletry formulations, geological drilling lubricants and aids, agrochemical compositions, paints, leathers, wood, metalworking fluids, industrial process aid formulations, cooling tower water, waste water, pasteurizers, tanning liquors, starch, dyes, petrochemicals, surfactants, defoamers, emulsions or water containing polymers, lipid based materials, carbohydrate based materials, proteinaceous materials, acrylic latex paint emulsions, and textiles.

The composition can also be useful in agrochemical formulations for the purpose of protecting seeds or crops against microbial spoilage.

Additional objects and advantages of the present invention will be set forth in part in the description which follows, and in part will be apparent from the description, or may be learned by the practice of the present invention. The objects and advantages of the present invention may be realized and obtained by means of the elements and combinations particularly pointed out in the claims.

It is to be understood that both the foregoing general description and the following general description are exemplary and explanatory only and are not restrictive of the present invention as claimed.

When two chemical microbicides are combined into one product or added separately three results are possible:

1) The resulting product would produce an additive (neutral) effect.

2) The products in the product would produce an antagonistic effect, or

3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

The microbicidal compositions combining a 1-hydroxymethylpyrazole and at least one preservative demonstrate an unexpected synergistic effect compared to the respective components alone. Thus, these compositions achieve superior, i.e. greater than additive, microbicidal activity at low concentrations against a wide variety of microorganisms. Examples of microorganisms include, but are not limited to, fungi and bacteria such as *Aspergillus niger* (ATCC 9642) and *Pseudomonas aeruginosa* (ATCC 15442). Preferably, the compositions of the present invention have a low toxicity.

The 1-hydroxymethylpyrazole is a compound having the formula

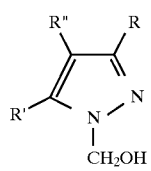

wherein R and R' are independently selected from hydrogen and alkyl of 1 to 4 carbon atoms, R" is a moiety selected from the group consisting of (a) hydrogen, (b) a halogen atom selected from the group consisting of F, Cl, Br, and I, and (c) a nitro group, or the hydrochloride salt of said compound.

The preparation of 1-hydroxymethylpyrazole is described in U.S. Pat. Nos. 4,801,361 and 5,335,432, and references referred to in these patents, all of which are incorporated herein by reference. 3,5-dimethyl-1-hydroxymethylpyrazole is commercially available and sold under the tradename Busan® 1504 or Busan® 1104 (Buckman Laboratories International, Memphis, Tenn.) and also easily synthesized from commercially available raw materials.

As described in Buckman Laboratories' Product Profile and Analytical Method (1992) for Busan® 1504 (both incorporated herein in their entirety by reference), Busan® 1504 is a broad-spectrum, nonionic bactericide and fungicide developed for the preservation of aqueous and aqueous-emulsified systems. Busan® 1504 is active over a broad pH range and is stable under both alkaline and acidic conditions. In addition, Busan® 1504 can be formulated into cationic, anionic, and nonionic systems. Busan® 1504 is also compatible with proteins. Busan® 1504 is a water-soluble, crystalline solid having 1-hydroxymethyl-3,5-dimethyl pyrazole as an active ingredient.

The preservative can be any preservative that will produce a synergistic effect when combined with a 1-hydroxymethylpyrazole. Examples include hexahydro-1,3,5-tris(2-hydroxyethyl)-s-triazine, bis 1,4-(bromoacetoxy)-2-butene; 2-bromo-2-nitropropane-1,3 diol; dimethylhydantoin; imidazolididinyl urea (also known as N,N$^1$-methylene bis(N$^1$-[1-hydroxy methyl)-2,5-dioxo-4-imidazolidinyl] urea); diazolidinyl urea (also known as N-(hydroxymethyl)-N-(1,3-dihydroxymethyl-2-5-dioxo-4-imidozolidinyl)-N-(hydroxymethyl) urea); mixture of 5-chloro-2-methyl-4-iso-thiazoline-3-one and 2-methyl-4-iso-thiazoline-3-one; 1-(3-chloroallyl)-3,5,7-triaza-1-azoniaadamantane chloride; and $C_1$–$C_6$ alkyl hydroxybenzoate. Further, mixtures of these preservatives can also be used. When such mixtures are used in combination with dimethylhydroxymethylpyrazole, at least one of the preservatives in the mixtures has a synergistic relationship with the dimethylhydroxymethylpyrazole. Preservatives useful in the invention are commercially available or may be synthesized from commercially available raw materials. Examples of commercially available preservatives include, but are not limited to, Busan® 1210 (bis 1,4-(bromoacetoxy)-2-butene—available from Buckman Laboratories International), Kathon CG (mixture of 5-chloro-2-methyl-4-isothiazoline-3-one and 2-methyl-4-isothiazoline-3-one—available from Rohm & Haas), Dowicil 200 (CIS isomer of 1-(3-chloroallyl)-3,5,7-triaza-1-azonia adamantane chloride—available from Dow Chemical Co.), Propyl Paraben ($C_1$–$C_6$ alkyl hydroxybenzoate—available from various sources), Busan® 1506 (hexahydro-1,3,5-tris(2-hydroxy-ethyl) -5-triazine—available from Buckman Laboratories International), Sodium Omadine (sodium 2-pyridinethiol -1-oxide—available from Olin Chemical Co.), Germall II (N-(hydroxymethyl)-N-C1,3-dihydroxymethyl-2-5-dioxo-4-imidozolidinyl)-N-(hydroxymethyl) urea or diazolidinyl urea—available from Sutton Laboratories), Bronopol (2-bromo-2-nitropropane-1,3 diol—available from Boots Chemical, and Glydant (dimethyl hydantoin—available from Sutton Laboratories).

The preservative may be chosen based on the compatibility with the materials or media. Compatibility is determined by criteria such as solubility in the fluid system and lack of reactivity with the fluid, material, or media in question. In view of the present invention, the compatibility is readily determined by one having ordinary skill in the art by adding (e.g., applying on the surface, incorporating in the fluid, material or media, and the like) the preservative to the material or media to be used. When used in a fluid system it is preferable that the preservative be freely soluble in the particular fluid resulting in a uniform solution or dispersion.

As these terms are used herein, "preventing" (which includes mitigating) spoilage is to be understood that the present invention in effect "controls" the growth of at least one microorganism, responsible, at least in part, for the spoilage. It is to be further understood that by "controlling" (i.e., preventing), the growth of at least one of these types of microorganisms is inhibited. In other words, there is no growth or essentially no growth of at least one microorganism. "Controlling" the growth of at least one microorganism maintains the microorganism population at a desired level, reduces the population to a desired level (even to undetectable limits, e.g., zero population), and/or inhibits the growth of the microorganism. Thus, the substrates or materials susceptible to attack by these types of microorganisms are preserved from this attack and the resulting spoilage and other detrimental effects caused by the microorganisms. Further, it is also to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated.

In the following discussion of preferred embodiments, component (a) is 3,5,-dimethyl 1-hydroxymethylpyrazole and component (b) is a preservative.

As described above, components (a) and (b) are used in synergistically effective amounts. The weight ratios of (a) to (b) vary depending on the type of microorganisms, material, or media to which the composition is applied. Generally, the ratio of component (a) to component (b) preferably ranges from 0.1 to 99, more preferably from 1:30 to 30:1, and most preferably from 1:5 to 5:1.

The following weight ratios of dimethylhydroxymethylpyrazole to the following preservatives are also preferred:

| | |
|---|---|
| Busan ® 1504:Busan ® 1210 | 80:0.01 to 1:2 |
| Busan ® 1504:Kathon CG ® | 80:1 to 1:2 |
| Busan ® 1504:Dowicil 200 ™ | 10:1 to 1:20 |
| Busan ® 1504:Propyl Paraben | 8:1 to 1:10 |
| Busan ® 1504:Methyl Paraben | 8:1 to 1:80 |
| Busan ® 1504:Busan ® 1506 | 16:1 to 1:30 |
| Busan ® 1504:Sodium Omadine | 50:0.1 to 1:10 |
| Busan ® 1504:Germall II ® | 4:1 to 0.1:25 |
| Busan ® 1504:Germall 115 ® | 0.8:1 to 0.1:16 |
| Busan ® 1504:Bronopol ® | 80:1 to 1:60 |
| Busan ® 1504:Glydant ® | 7:1 to 0.1:25 |

Depending upon the specific application, the composition may be prepared in liquid form by dissolving the composition in an organic solvent. The preservative may be prepared in an emulsion form by emulsifying it in water, or if necessary, by adding a surfactant. Additional chemicals such as corrosion inhibitors, performing agents, and insecticides may be added to the foregoing preparation.

The synergistic activity of the combinations described above has been confirmed using standard laboratory techniques as illustrated below. The following examples are intended to illustrate, not limit, the present invention.

Microbioloaical evaluation

A. Fungal evaluation

Mineral salts-glucose medium was used. To prepare the medium, the following ingredients were added to 1 liter of deionized water: 0.7 g of $KH_2PO_4$, 0.7 g of $MgSO_4 \cdot 7H_2O$, 1.0 g of $NH_4NO_3$, 0.005 g NaCl, 0.002 g $FeSO_4 \cdot 7H_2O$, 0.002 g $ZnSO_4 \cdot 7H_2O$, 0.001 g $MnSO_4 \cdot 7H_2O$, 10 g of Glucose. The pH of the medium was adjusted to 6 with 1N NaOH. The medium was distributed in 5.0 ml amounts in test tubes and autoclaved at 121° C. for 20 minutes. The fungus, A. *niger*, was grown on a potato dextrose agar slant for 7 to 10 days and a spore suspension prepared by washing down the spores from the slant into a sterile saline solution. After addition of the biocides in the desired concentrations to the sterile mineral salts-glucose medium, the fungal spore suspension was added (0.1 ml of inoculum). The final spore concentration was approximately $10^6$ cfu/mL. The inoculated media was incubated at 28° C. for 10–14 days.

B. Bacterial evaluation

Nutrient broth growth medium was used. To prepare the medium, the following ingredients were added to one liter of deionized water: 8.0 g NaCl, 1.0 g glucose, and 1.0 g tryptone. The pH of the medium was adjusted to 6 with 1 N HCL. This was distributed in 5 mL amounts in test tubes and autoclaved for 20 minutes at 121° C. After addition of the biocides in the desired concentrations to the nutrient broth, 100 microliters of a suspension of *Pseudomonas aeruginosa* cells of approximately $10^6$ cfc/mL were added and incubated at 37° C. for 5–7 days.

In the Examples, a synergistic effect was demonstrated in separate experiments by testing 3,5,-dimethyl - 1-hydroxymethylpyrazole, designated as component A and the corresponding preservative or its salt as component B in a series of tests in varying ratios and a range of concentrations against the fungus, *Aspergillus niger* and also against the bacterium, *Pseudomonas aeruginosa* using the methods described above.

The lowest concentration of each mixture or compound which completely prevented growth of the fungus for about two weeks (10–14 days) and the bacterium for about one week (5–7 days) was taken as the end points for synergism calculations. End points for the various mixtures were then compared with the end points for the pure active ingredients alone in concomitantly prepared flasks or test tubes.

Synergism was demonstrated by the method described by Kull, E. C., Eisman, P. C., Sylwestrwicz, H. D., and Mayer, R. L. 1961. Applied Microbiology. 9: 538-541 wherein QA/Qa+QB/Qb is less than 1

Qa (Busan® 1504)=Concentration of compound A in parts per million, acting alone, which produced an end point.

Qb (preservative)=Concentration of compound B in parts per million, acting alone, which produced an end point.

QA (Busan® 1504)=Concentration of compound A in parts per million, in the mixture, which produced an end point.

QB (preservative)=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, which is incorporated herein by reference.

In general, however, an effective fungicidal and bactericidal response can be obtained when the synergistic combination is employed in concentrations ranging from about 0.1 to about 10,000 ppm of a 1-hydroxymethylpyrazole, preferably about 0.1 to about 5,000 ppm, and most preferably about 1 to about 2,000 ppm, and from about 0.1 to about 10,000 ppm of a preservative, preferably about 0.1 to about 5,000 ppm and most preferably about 1 to about 3,000 ppm.

TABLE 1

Summary of Synergism in Antibacterial Test (vs *Ps. aeruginosa*)

| Combination | Synergism | SI Range* |
|---|---|---|
| BS1504 + BS1210 | yes | 0.48–0.75 |
| B51504 + Kathon CC | yes | 0.58–0.75 |
| BS1504 + Dowicil 200 | yes | 0.79–0.93 |
| BS1504 + Propyl Paraben | yes | 0.67–0.83 |
| BS1504 + Methyl Paraben | yes | 0.68–0.92 |
| B51504 + BS1506 | yes | 0.70–0.97 |
| BS1504 + Sodium Omadine | yes | 0.68–0.98 |
| BS1504 + Germall II | yes | 0.73–0.98 |
| BS1504 + Germall 115 | yes | 0.77–0.96 |
| BS1504 + Bronopol | yes | 0.75–0.96 |
| BS1504 + Glydant | yes | 0.75–0.96 |

TABLE 2

Summary of Synergism in Antifungal Test (vs *A. niger*)

| Combination | Synergism | SI Range |
|---|---|---|
| BS1504 + BS1210 | yes | 0.48–0.75 |
| BS1504 + Kathon CC | yes | 0.79–0.96 |
| BS1504 + Dowicil 200 | yes | 0.55–0.77 |
| BS1504 + Propyl Paraben | no | — |
| BS1504 + Methyl Paraben | no | — |
| BS1504 + BS1506 | yes | 0.67–0.93 |
| BS1504 + Sodium Omadine | yes | 0.34–0.77 |
| BS1504 + Germall II | yes | 0.73–0.97 |
| BS1504 + Germall 115 | no | — |
| BS1504 + Bronopol | yes | 0.69–0.93 |
| BS1504 + Glydant | yes | 0.68–0.97 |

*SI = I (additive) or SI > 1 (antagonistic) were not included.

TABLE 3

Combination of Busan 1504 with Busan 1210 vs *Ps. aeruginosa*

| BS1504 (ppm) | BS1210 (ppm) | Growth | SI | BS1504 (ppm) | BS1210 (ppm) | Growth | SI |
|---|---|---|---|---|---|---|---|
| 10 | 0 | + |  | 30 | 1 | + |  |
| 20 | 0 | + |  | 30 | 2 | + |  |
| 40 | 0 | + |  | 30 | 5 | + |  |
| 80 | 0 | + |  | 30 | 10 | + |  |
| 100 | 0 | + |  | 30 | 20 | + |  |
| 120 | 0 | − |  | 40 | 1 | + |  |
| 140 | 0 | − |  | 40 | 2 | + |  |
| 160 | 0 | − |  | 40 | 5 | + |  |
| 180 | 0 | − |  | 40 | 10 | + |  |
| 200 | 0 | − |  | 40 | 20 | − | 0.58 |
| 0 | 10 | + |  | 50 | 1 | + |  |
| 0 | 20 | + |  | 50 | 2 | + |  |
| 0 | 30 | + |  | 50 | 5 | − | 0.48 |
| 0 | 40 | + |  | 50 | 10 | − |  |

TABLE 3-continued

Combination of Busan 1504 with Busan 1210
vs *Ps. aeruginosa*

| BS1504 (ppm) | BS1210 (ppm) | Growth | SI | BS1504 (ppm) | BS1210 (ppm) | Growth | SI |
|---|---|---|---|---|---|---|---|
| 0 | 50 | + |  | 50 | 20 | − |  |
| 0 | 60 | + |  | 60 | 1 | + |  |
| 0 | 80 | − |  | 60 | 2 | + |  |
| 0 | 100 | − |  | 60 | 5 | − | 0.56 |
| 10 | 2 | + |  | 60 | 10 | − |  |
| 10 | 5 | + |  | 60 | 20 | − |  |
| 10 | 10 | + |  | 70 | 1 | + |  |
| 10 | 20 | + |  | 70 | 2 | + |  |
| 20 | 2 | + |  | 70 | 5 | − | 0.65 |
| 20 | 5 | + |  | 70 | 10 | − |  |
| 20 | 10 | + |  | 70 | 20 | − |  |
| 20 | 20 | + |  |  |  |  |  |

TABLE 4

Combination of Busan 1504 with Busan 1210
vs *A. niger*

| BS1504 (ppm) | BS1210 (ppm) | Growth | SI | BS1504 (ppm) | BS1210 (ppm) | Growth | SI |
|---|---|---|---|---|---|---|---|
| 300 | 0 | + |  | 100 | 0.2 | + |  |
| 400 | 0 | + |  | 100 | 0.4 | + |  |
| 500 | 0 | + |  | 100 | 0.6 | + |  |
| 600 | 0 | − |  | 100 | 0.8 | − | 0.27 |
| 700 | 0 | − |  | 100 | 1.0 | − |  |
| 800 | 0 | − |  | 100 | 1.5 | − |  |
| 0 | 0.2 | + |  | 100 | 2.0 | − |  |
| 0 | 0.5 | + |  | 200 | 0.1 | + |  |
| 0 | 0.8 | + |  | 200 | 0.2 | + |  |
| 0 | 1 | + |  | 200 | 0.4 | − | 0.38 |
| 0 | 2 | + |  | 200 | 0.6 | − |  |
| 0 | 4 | + |  | 200 | 0.8 | − |  |
| 0 | 8 | − |  | 200 | 1.0 | − |  |
| 0 | 16 | − |  | 200 | 1.5 | − |  |
| 10 | 0.2 | + |  | 300 | 0.1 | − | 0.51 |
| 10 | 0.5 | + |  | 300 | 0.2 | − |  |
| 10 | 0.8 | + |  | 300 | 0.4 | − |  |
| 10 | 1.0 | + |  | 300 | 0.6 | − |  |
| 10 | 1.5 | + |  | 300 | 0.8 | − |  |
| 10 | 2.0 | − | 0.27 | 300 | 1.0 | − |  |
| 10 | 4.0 | − |  | 300 | 1.5 | − |  |
| 50 | 0.2 | + |  | 400 | 0.05 | − | 0.67 |
| 50 | 0.5 | + |  | 400 | 0.1 | − |  |
| 50 | 0.8 | + |  | 400 | 0.2 | − |  |
| 50 | 1.0 | − | 0.21 | 400 | 0.4 | − |  |
| 50 | 1.5 | − |  | 400 | 0.6 | − |  |
| 50 | 2.0 | − |  | 400 | 0.8 | − |  |
| 50 | 4.0 | − |  | 400 | 1.0 | − |  |
|  |  |  |  | 400 | 1.5 | − |  |

TABLE 5

Combination of Busan 1504 with Kathon CG
vs *Ps. aeruginosa*

| BS1504 (ppm) | KN CG (ppm) | Growth | SI | BS1504 (ppm) | KN CG (ppm) | Growth | SI |
|---|---|---|---|---|---|---|---|
| 10 | 0 | + |  | 30 | 1 | + |  |
| 20 | 0 | + |  | 30 | 2 | + |  |
| 40 | 0 | + |  | 30 | 5 | + |  |
| 80 | 0 | + |  | 30 | 10 | − | 0.75 |
| 100 | 0 | + |  | 30 | 20 | − |  |
| 120 | 0 | − |  | 40 | 1 | + |  |
| 140 | 0 | − |  | 40 | 2 | + |  |
| 160 | 0 | − |  | 40 | 5 | − | 0.58 |
| 180 | 0 | − |  | 40 | 10 | − |  |
| 200 | 0 | − |  | 40 | 20 | − |  |
| 0 | 10 | + |  | 50 | 1 | + |  |
| 0 | 20 | − |  | 50 | 2 | + |  |
| 0 | 30 | − |  | 50 | 5 | − | 0.67 |
| 0 | 40 | − |  | 50 | 10 | − |  |
| 0 | 50 | − |  | 50 | 20 | − |  |
| 0 | 60 | − |  | 60 | 1 | + |  |
| 0 | 80 | − |  | 60 | 2 | + |  |
| 0 | 100 | − |  | 60 | 5 | − | 0.75 |
| 10 | 2 | + |  | 60 | 10 | − |  |
| 10 | 5 | + |  | 60 | 20 | − |  |
| 10 | 10 | + |  | 70 | 1 | + |  |
| 10 | 20 | − |  | 70 | 2 | − | 0.68 |
| 20 | 2 | + |  | 70 | 5 | − |  |
| 20 | 5 | + |  | 70 | 10 | − |  |
| 20 | 10 | − | 0.67 | 70 | 20 | − |  |
| 20 | 20 | − |  |  |  |  |  |

TABLE 6

Combination of Busan 1504 with Kathon CG
vs *A. niger*

| BS1504 (ppm) | KN CG (ppm) | Growth | SI | BS1504 (ppm) | KN CG (ppm) | Growth | SI |
|---|---|---|---|---|---|---|---|
| 300 | 0 | + |  | 200 | 5 | + |  |
| 400 | 0 | + |  | 200 | 10 | + |  |
| 500 | 0 | + |  | 200 | 15 | + |  |
| 600 | 0 | + |  | 200 | 20 | + |  |
| 700 | 0 | + |  | 200 | 25 | − | 0.87 |
| 800 | 0 | − |  | 200 | 30 | − |  |
| 0 | 10 | + |  | 200 | 35 | − |  |
| 0 | 20 | + |  | 300 | 5 | + |  |
| 0 | 30 | + |  | 300 | 10 | + |  |
| 0 | 40 | − |  | 300 | 15 | + |  |
| 0 | 50 | − |  | 300 | 20 | − | 0.87 |
| 0 | 60 | − |  | 300 | 25 | − |  |
| 0 | 70 | − |  | 300 | 30 | − |  |
| 0 | 80 | − |  | 300 | 35 | − |  |
| 10 | 10 | + |  | 400 | 1 | + |  |
| 10 | 20 | + |  | 400 | 2 | + |  |
| 10 | 30 | + |  | 400 | 4 | + |  |
| 10 | 40 | + |  | 400 | 8 | + |  |
| 50 | 10 | + |  | 400 | 16 | − | 0.90 |
| 50 | 20 | + |  | 400 | 20 | − |  |
| 50 | 30 | + |  | 400 | 25 | − |  |
| 50 | 40 | − |  | 400 | 30 | − |  |
| 100 | 10 | + |  | 500 | 1 | + |  |
| 100 | 20 | + |  | 500 | 2 | + |  |
| 100 | 30 | − | 0.87 | 500 | 4 | + |  |
| 100 | 40 | − |  | 500 | 8 | + |  |
|  |  |  |  | 500 | 16 | − |  |
|  |  |  |  | 500 | 20 | − |  |
|  |  |  |  | 500 | 25 | − |  |

TABLE 7

Combination of Busan 1504 with Dowicil 200
vs *Ps. aeruginosa*

| BS1504 (ppm) | DW200 (ppm) | Growth | SI | BS1504 (ppm) | DW200 (ppm) | Growth | SI |
|---|---|---|---|---|---|---|---|
| 10 | 0 | + |  | 30 | 10 | + |  |
| 20 | 0 | + |  | 30 | 20 | + |  |
| 40 | 0 | + |  | 30 | 30 | + |  |
| 80 | 0 | − |  | 30 | 40 | + |  |

TABLE 7-continued

Combination of Busan 1504 with Dowicil 200 vs *Ps. aeruginosa*

| BS1504 (ppm) | DW200 (ppm) | Growth | SI | BS1504 (ppm) | DW200 (ppm) | Growth | SI |
|---|---|---|---|---|---|---|---|
| 100 | 0 | − | | 30 | 50 | + | |
| 120 | 0 | − | | 30 | 60 | + | |
| 140 | 0 | − | | 30 | 70 | + | |
| 160 | 0 | − | | 40 | 10 | + | |
| 180 | 0 | − | | 40 | 20 | + | |
| 200 | 0 | − | | 40 | 20 | + | |
| 0 | 100 | + | | 40 | 40 | + | |
| 0 | 110 | + | | 40 | 50 | + | |
| 0 | 120 | + | | 40 | 60 | + | |
| 0 | 130 | + | | 50 | 10 | + | |
| 0 | 140 | + | | 50 | 20 | + | |
| 0 | 150 | + | | 50 | 30 | − | 0.79 |
| 0 | 160 | + | | 50 | 40 | + | |
| 0 | 180 | − | | 50 | 50 | − | 0.90 |
| 10 | 30 | + | | 50 | 60 | − | |
| 10 | 40 | + | | 60 | 10 | + | |
| 10 | 50 | + | | 60 | 20 | − | 0.86 |
| 10 | 60 | + | | 60 | 30 | − | |
| 10 | 70 | + | | 60 | 40 | − | |
| 20 | 20 | + | | 60 | 50 | − | |
| 20 | 30 | + | | 60 | 60 | + | |
| 20 | 40 | + | | 70 | 10 | − | 0.93 |
| 20 | 50 | + | | 70 | 20 | − | |
| 20 | 60 | + | | 70 | 30 | − | |
| 20 | 70 | + | | 70 | 40 | − | |

TABLE 8

Combination of Busan 1504 with Dowicil 200 vs *A. Niger*

| BS1504 (ppm) | DW200 (ppm) | Growth | SI | BS1504 (ppm) | DW200 (ppm) | Growth | SI |
|---|---|---|---|---|---|---|---|
| 300 | 0 | + | | 200 | 20 | + | |
| 400 | 0 | + | | 200 | 50 | + | |
| 500 | 0 | + | | 200 | 80 | − | 0.55 |
| 600 | 0 | + | | 200 | 100 | − | |
| 700 | 0 | − | | 200 | 120 | − | |
| 800 | 0 | − | | 200 | 150 | − | |
| 0 | 100 | + | | 200 | 200 | − | |
| 0 | 200 | + | | 200 | 250 | − | |
| 0 | 300 | − | | 200 | 300 | − | |
| 0 | 400 | − | | 300 | 10 | + | |
| 0 | 500 | − | | 300 | 20 | + | |
| 0 | 600 | − | | 300 | 40 | + | |
| 10 | 50 | + | | 300 | 60 | − | 0.63 |
| 10 | 100 | + | | 300 | 80 | − | |
| 10 | 200 | − | 0.68 | 300 | 100 | − | |
| 10 | 250 | − | | 300 | 120 | − | |
| 10 | 300 | − | | 300 | 150 | − | |
| 50 | 50 | + | | 300 | 200 | − | |
| 50 | 100 | + | | 400 | 10 | + | |
| 50 | 150 | + | | 400 | 20 | + | |
| 50 | 200 | − | 0.74 | 400 | 40 | + | |
| 50 | 250 | − | | 400 | 60 | − | 0.77 |
| 50 | 300 | − | | 400 | 80 | − | |
| 100 | 50 | + | | 400 | 100 | − | |
| 100 | 100 | + | | 400 | 120 | − | |
| 100 | 150 | − | 0.64 | 400 | 150 | − | |
| 100 | 200 | − | | 400 | 200 | − | |
| 100 | 250 | − | | | | | |
| 100 | 300 | − | | | | | |

TABLE 9

Combination of Busan 1504 and Propyl Paraben vs *Ps. aeruginosa*

| BS1504 (ppm) | PPB (ppm) | Growth | SI | BS1504 (ppm) | PPB (ppm) | Growth | SI |
|---|---|---|---|---|---|---|---|
| 40 | 0 | + | | 40 | 500 | + | |
| 60 | 0 | + | | 40 | 600 | + | |
| 80 | 0 | + | | 40 | 700 | − | 0.80 |
| 100 | 0 | + | | 40 | 800 | − | |
| 120 | 0 | − | | 50 | 200 | + | |
| 140 | 0 | − | | 50 | 300 | + | |
| 160 | 0 | − | | 50 | 400 | + | |
| 180 | 0 | − | | 50 | 500 | − | 0.75 |
| 0 | 200 | + | | 50 | 600 | − | |
| 0 | 400 | + | | 50 | 700 | − | |
| 0 | 600 | + | | 60 | 100 | + | |
| 0 | 800 | + | | 60 | 200 | + | |
| 0 | 900 | + | | 60 | 300 | + | |
| 0 | 1000 | + | | 60 | 400 | − | 0.77 |
| 0 | 1200 | + | | 60 | 500 | − | |
| 0 | 1500 | − | | 60 | 600 | − | |
| 0 | 2000 | − | | 70 | 50 | + | |
| 10 | 700 | + | | 70 | 100 | + | |
| 10 | 800 | + | | 70 | 200 | − | 0.72 |
| 10 | 900 | + | | 70 | 300 | − | |
| 20 | 600 | + | | 70 | 400 | − | |
| 20 | 700 | + | | 70 | 500 | − | |
| 20 | 800 | + | | 80 | 10 | − | 0.67 |
| 20 | 900 | + | | 80 | 20 | − | |
| 30 | 500 | + | | 80 | 40 | − | |
| 30 | 600 | + | | 80 | 60 | − | |
| 30 | 700 | − | 0.72 | 80 | 80 | − | |
| 30 | 800 | − | | 80 | 100 | − | |
| | | | | 80 | 200 | − | |
| | | | | 80 | 300 | − | |

TABLE 10

Combination of Busan 1504 with Propyl Paraben vs *A. niger*

| BS1504 (ppm) | PPB (ppm) | Growth | SI | BS1504 (ppm) | PPB (ppm) | Growth | SI |
|---|---|---|---|---|---|---|---|
| 300 | 0 | + | | 200 | 10 | + | |
| 400 | 0 | + | | 200 | 20 | + | |
| 500 | 0 | + | | 200 | 40 | + | |
| 600 | 0 | + | | 200 | 60 | + | |
| 700 | 0 | − | | 200 | 80 | + | |
| 800 | 0 | − | | 200 | 100 | + | |
| 0 | 50 | + | | 200 | 150 | + | |
| 0 | 100 | + | | 300 | 10 | + | |
| 0 | 150 | + | | 300 | 20 | + | |
| 0 | 200 | − | | 300 | 40 | + | |
| 0 | 250 | − | | 300 | 60 | + | |
| 0 | 300 | − | | 300 | 80 | + | |
| 0 | 400 | − | | 300 | 100 | + | |
| 0 | 500 | − | | 400 | 10 | + | |
| 10 | 50 | + | | 400 | 20 | + | |
| 10 | 80 | + | | 400 | 40 | + | |
| 10 | 100 | + | | 400 | 60 | + | |
| 10 | 150 | + | | 400 | 80 | + | |
| 50 | 50 | + | | 400 | 100 | + | |
| 50 | 80 | + | | | | | |
| 50 | 100 | + | | | | | |
| 50 | 150 | + | | | | | |
| 100 | 10 | + | | | | | |
| 100 | 20 | + | | | | | |
| 100 | 40 | + | | | | | |
| 100 | 60 | + | | | | | |
| 100 | 80 | + | | | | | |
| 100 | 100 | + | | | | | |
| 100 | 150 | + | | | | | |

TABLE 11

Combination of Busan 1504 and Methyl Paraben vs Ps. aeruginosa

| BS1504 (ppm) | MPB (ppm) | Growth | SI | BS1504 (ppm) | MPB (ppm) | Growth | SI |
|---|---|---|---|---|---|---|---|
| 40 | 0 | + | | 30 | 400 | + | |
| 60 | 0 | + | | 30 | 500 | − | 1.07 |
| 80 | 0 | + | | 30 | 600 | − | |
| 100 | 0 | + | | 30 | 700 | − | |
| 120 | 0 | − | | 30 | 800 | − | |
| 140 | 0 | − | | 40 | 300 | + | |
| 160 | 0 | − | | 40 | 400 | + | |
| 180 | 0 | − | | 40 | 500 | − | 1.15 |
| 0 | 200 | + | | 40 | 600 | − | |
| 0 | 400 | + | | 40 | 700 | − | |
| 0 | 500 | + | | 50 | 300 | + | |
| 0 | 600 | − | | 50 | 400 | + | |
| 0 | 700 | − | | 50 | 500 | + | |
| 0 | 800 | − | | 50 | 600 | + | |
| 0 | 900 | − | | 50 | 700 | − | 1.56 |
| 0 | 1000 | − | | 60 | 200 | + | |
| 0 | 1500 | − | | 60 | 300 | + | |
| 10 | 400 | + | | 60 | 400 | + | |
| 10 | 500 | + | | 60 | 500 | + | |
| 10 | 600 | − | 1.08 | 60 | 600 | − | 1.50 |
| 10 | 700 | − | | 70 | 50 | + | |
| 10 | 800 | − | | 70 | 100 | + | |
| 10 | 900 | − | | 70 | 200 | + | |
| 20 | 400 | + | | 70 | 300 | + | |
| 20 | 500 | + | | 70 | 400 | + | |
| 20 | 600 | − | 1.16 | 70 | 500 | − | 1.41 |
| 20 | 700 | − | | 80 | 10 | + | |
| 20 | 800 | − | | 80 | 20 | + | |
| | | | | 80 | 50 | + | |
| | | | | 80 | 100 | + | |
| | | | | 80 | 200 | + | |
| | | | | 80 | 300 | + | |

TABLE 12

Combination of Busan 1504 and Methyl Paraben vs A. niger

| BS1504 (ppm) | MPB (ppm) | Growth | SI | BS1504 (ppm) | MPB (ppm) | Growth | SI |
|---|---|---|---|---|---|---|---|
| 300 | 0 | + | | 200 | 100 | + | |
| 400 | 0 | + | | 200 | 200 | + | |
| 500 | 0 | + | | 200 | 400 | + | |
| 600 | 0 | + | | 200 | 600 | + | |
| 700 | 0 | + | | 200 | 800 | − | 1.25 |
| 800 | 0 | − | | 300 | 50 | + | |
| 0 | 200 | + | | 300 | 100 | + | |
| 0 | 400 | + | | 300 | 200 | + | |
| 0 | 600 | + | | 300 | 400 | + | |
| 0 | 500 | − | | 300 | 600 | + | |
| 0 | 1000 | − | | 300 | 800 | − | 1.37 |
| 0 | 2000 | − | | 400 | 50 | + | |
| 10 | 200 | + | | 400 | 100 | + | |
| 10 | 400 | + | | 400 | 200 | + | |
| 10 | 600 | + | | 400 | 400 | + | |
| 10 | 800 | − | 1.01 | 400 | 600 | − | 1.25 |
| 10 | 1000 | − | | 400 | 800 | + | |
| 50 | 200 | + | | 500 | 10 | + | |
| 50 | 400 | + | | 500 | 50 | + | |
| 50 | 600 | + | | 500 | 100 | + | |
| 50 | 800 | − | 1.06 | 500 | 200 | + | |
| 50 | 1000 | − | | 500 | 400 | + | |
| 100 | 100 | + | | 500 | 600 | − | 1.37 |
| 100 | 200 | + | | 600 | 10 | + | |
| 100 | 400 | + | | 600 | 50 | + | |
| 100 | 600 | + | | 600 | 100 | + | |
| 100 | 800 | − | 1.13 | 600 | 200 | + | |
| | | | | 600 | 400 | + | |
| | | | | 600 | 600 | − | 1.50 |

TABLE 13

Combination of Busan 1504 with Busan 1506 vs Ps. aeruginosa

| BS1504 (ppm) | BS1506 (ppm) | Growth | SI | BS1504 (ppm) | BS1506 (ppm) | Growth | SI |
|---|---|---|---|---|---|---|---|
| 40 | 0 | + | | 20 | 10 | + | |
| 60 | 0 | + | | 20 | 20 | + | |
| 80 | 0 | + | | 20 | 30 | + | |
| 100 | 0 | + | | 20 | 40 | + | |
| 120 | 0 | + | | 20 | 50 | + | |
| 140 | 0 | − | | 20 | 60 | + | |
| 160 | 0 | − | | 20 | 70 | − | 0.73 |
| 180 | 0 | − | | 30 | 5 | + | |
| 0 | 20 | + | | 30 | 10 | + | |
| 0 | 40 | + | | 30 | 20 | + | |
| 0 | 60 | + | | 30 | 30 | + | |
| 0 | 80 | + | | 30 | 40 | + | |
| 0 | 100 | + | | 30 | 50 | + | |
| 0 | 120 | − | | 30 | 60 | + | |
| 0 | 140 | − | | 40 | 1 | + | |
| 0 | 160 | − | | 40 | 5 | + | |
| 0 | 180 | − | | 40 | 10 | + | |
| 0 | 200 | − | | 40 | 20 | + | |
| 5 | 10 | + | | 40 | 30 | + | |
| 5 | 20 | + | | 40 | 40 | + | |
| 5 | 30 | + | | 40 | 50 | + | |
| 5 | 40 | + | | 50 | 1 | + | |
| 5 | 50 | + | | 50 | 5 | + | |
| 5 | 60 | + | | 50 | 10 | + | |
| 5 | 70 | + | | 50 | 20 | + | |
| 5 | 80 | − | 0.70 | 50 | 30 | + | |
| 10 | 20 | + | | 50 | 40 | + | |
| 10 | 30 | + | | | | | |
| 10 | 40 | + | | | | | |
| 10 | 50 | + | | | | | |
| 10 | 60 | + | | | | | |
| 10 | 70 | + | | | | | |
| 10 | 80 | + | | | | | |

TABLE 14

Combination of Busan 1504 with Busan 1506 vs A. niger

| BS1504 (ppm) | BS1506 (ppm) | Growth | SI | BS1504 (ppm) | BS1506 (ppm) | Growth | SI |
|---|---|---|---|---|---|---|---|
| 300 | 0 | + | | 200 | 50 | + | |
| 400 | 0 | + | | 200 | 100 | + | |
| 500 | 0 | + | | 200 | 150 | + | |
| 600 | 0 | + | | 200 | 200 | + | |
| 700 | 0 | − | | 200 | 250 | − | 0.91 |
| 800 | 0 | − | | 200 | 300 | − | |
| 0 | 100 | + | | 300 | 20 | + | |
| 0 | 200 | + | | 300 | 40 | + | |
| 0 | 300 | + | | 300 | 60 | + | |
| 0 | 400 | − | | 300 | 80 | + | |
| 0 | 500 | − | | 300 | 100 | + | |
| 0 | 600 | − | | 300 | 150 | + | |
| 10 | 100 | + | | 300 | 200 | − | 0.93 |
| 10 | 200 | + | | 300 | 250 | − | |

TABLE 14-continued

Combination of Busan 1504 with Busan 1506 vs *A. niger*

| BS1504 (ppm) | BS1506 (ppm) | Growth | SI | BS1504 (ppm) | BS1506 (ppm) | Growth | SI |
|---|---|---|---|---|---|---|---|
| 10 | 300 | − | 0.76 | 300 | 300 | − | |
| 10 | 400 | − | | 400 | 20 | + | |
| 50 | 100 | + | | 400 | 40 | + | |
| 50 | 200 | + | | 400 | 60 | + | |
| 50 | 300 | − | 0.82 | 400 | 80 | + | |
| 50 | 400 | − | | 400 | 100 | + | |
| 100 | 50 | + | | 400 | 150 | + | |
| 100 | 100 | + | | 400 | 200 | − | |
| 100 | 150 | + | | 400 | 250 | − | |
| 100 | 200 | + | | 400 | 300 | − | |
| 100 | 250 | − | 0.77 | | | | |
| 100 | 300 | − | | | | | |
| 100 | 400 | − | | | | | |

TABLE 15

Combination of Busan 1504 with Sodium Omadine vs *P. aeruginosa*

| BS1504 (ppm) | SOMD (ppm) | Growth | SI | BS1504 (ppm) | SOMD (ppm) | Growth | SI |
|---|---|---|---|---|---|---|---|
| 40 | 0 | + | | 40 | 10 | + | |
| 60 | 0 | + | | 40 | 20 | + | |
| 80 | 0 | + | | 40 | 40 | + | |
| 100 | 0 | + | | 40 | 60 | − | 0.93 |
| 120 | 0 | − | | 40 | 80 | − | |
| 140 | 0 | − | | 40 | 100 | − | |
| 160 | 0 | − | | 50 | 10 | + | |
| 180 | 0 | − | | 50 | 20 | + | |
| 0 | 20 | + | | 50 | 40 | − | 0.82 |
| 0 | 40 | + | | 50 | 60 | − | |
| 0 | 60 | + | | 50 | 80 | − | |
| 0 | 80 | + | | 50 | 100 | − | |
| 0 | 100 | − | | 60 | 10 | + | |
| 0 | 120 | − | | 60 | 20 | + | |
| 0 | 150 | − | | 60 | 40 | − | 0.90 |
| 0 | 200 | − | | 60 | 60 | − | |
| 0 | 300 | − | | 60 | 80 | − | |
| 10 | 40 | + | | 60 | 100 | − | |
| 10 | 60 | + | | 70 | 10 | − | 0.68 |
| 10 | 80 | + | | 70 | 20 | − | |
| 10 | 100 | − | | 70 | 30 | − | |
| 20 | 20 | + | | 70 | 40 | − | |
| 20 | 40 | + | | 70 | 50 | − | |
| 20 | 60 | − | 0.76 | 70 | 60 | − | |
| 20 | 80 | − | | 80 | 10 | − | 0.77 |
| 20 | 100 | − | | 80 | 20 | − | |
| 30 | 20 | + | | 80 | 30 | − | |
| 30 | 40 | + | | 80 | 40 | − | |
| 30 | 60 | − | 0.85 | 80 | 50 | − | |
| 30 | 80 | − | | 80 | 60 | − | |
| 30 | 100 | − | | | | | |

TABLE 16

Combination of Busan 1504 and Sodium Omadine vs *A. niger*

| BS1504 (ppm) | SOMD (ppm) | Growth | SI | BS1504 (ppm) | SOMD (ppm) | Growth | SI |
|---|---|---|---|---|---|---|---|
| 300 | 0 | + | | 200 | 0.2 | + | |
| 400 | 0 | + | | 200 | 0.5 | + | |
| 500 | 0 | + | | 200 | 1 | + | |
| 600 | 0 | + | | 200 | 2 | + | |
| 700 | 0 | + | | 200 | 4 | − | 0.65 |
| 800 | 0 | − | | 200 | 8 | − | |

TABLE 16-continued

Combination of Busan 1504 and Sodium Omadine vs *A. niger*

| BS1504 (ppm) | SOMD (ppm) | Growth | SI | BS1504 (ppm) | SOMD (ppm) | Growth | SI |
|---|---|---|---|---|---|---|---|
| 0 | 1 | + | | 200 | 16 | − | |
| 0 | 5 | + | | 300 | 0.2 | + | |
| 0 | 10 | − | | 300 | 0.5 | + | |
| 0 | 20 | − | | 300 | 1 | + | |
| 0 | 30 | − | | 300 | 2 | + | |
| 0 | 50 | − | | 300 | 4 | − | 0.77 |
| 0 | 80 | − | | 300 | 8 | − | |
| 0 | 160 | − | | 300 | 16 | − | |
| 10 | 1 | + | | 400 | 0.1 | + | |
| 10 | 5 | + | | 400 | 0.2 | + | |
| 10 | 10 | − | | 400 | 0.4 | + | |
| 10 | 20 | − | | 400 | 0.5 | + | |
| 50 | 1 | + | | 400 | 1 | + | |
| 50 | 5 | + | | 400 | 2 | − | 0.70 |
| 50 | 10 | − | | 400 | 4 | − | |
| 50 | 20 | − | | 400 | 8 | − | |
| 100 | 0.5 | + | | 400 | 16 | − | |
| 100 | 1 | + | | 500 | 0.1 | + | |
| 100 | 2 | + | | 500 | 0.2 | + | |
| 100 | 4 | − | 0.53 | 500 | 0.4 | + | |
| 100 | 8 | − | | 500 | 0.8 | + | |
| 100 | 16 | − | | 500 | 1 | − | 0.72 |
| | | | | 500 | 2 | − | |
| | | | | 500 | 4 | − | |
| | | | | 500 | 8 | − | |
| | | | | 500 | 16 | − | |

TABLE 17

Combination of Busan 1504 and Germall II vs *P. aeruginosa*

| BS1504 (ppm) | GII (ppm) | Growth | SI | BS1504 (ppm) | GII (ppm) | Growth | SI |
|---|---|---|---|---|---|---|---|
| 40 | 0 | + | | 40 | 50 | + | |
| 60 | 0 | + | | 40 | 80 | + | |
| 80 | 0 | + | | 40 | 100 | − | |
| 100 | 0 | + | | 40 | 120 | − | |
| 120 | 0 | − | | 40 | 140 | − | |
| 140 | 0 | − | | 40 | 160 | − | |
| 160 | 0 | − | | 50 | 20 | + | |
| 180 | 0 | − | | 50 | 40 | + | |
| 0 | 50 | + | | 50 | 80 | − | 0.98 |
| 0 | 80 | + | | 50 | 100 | − | |
| 0 | 100 | + | | 50 | 120 | − | |
| 0 | 120 | + | | 50 | 140 | − | |
| 0 | 140 | − | | 60 | 20 | + | |
| 0 | 160 | − | | 60 | 40 | + | |
| 0 | 180 | − | | 60 | 80 | − | |
| 0 | 200 | − | | 60 | 100 | − | |
| 10 | 100 | + | | 60 | 120 | − | |
| 10 | 120 | − | 0.94 | 60 | 140 | − | |
| 10 | 140 | − | | 70 | 20 | + | |
| 10 | 160 | − | | 70 | 40 | − | 0.87 |
| 10 | 180 | − | | 70 | 60 | − | |
| 20 | 100 | + | | 70 | 80 | − | |
| 20 | 120 | − | | 70 | 100 | − | |
| 20 | 140 | − | | 70 | 120 | − | |
| 20 | 160 | − | | 70 | 140 | − | |
| 20 | 180 | − | | 80 | 10 | + | |
| 30 | 50 | + | | 80 | 20 | − | 0.81 |
| 30 | 80 | + | | 80 | 40 | − | |
| 30 | 100 | − | 0.96 | 80 | 50 | − | |
| 30 | 120 | − | | 80 | 60 | − | |
| 30 | 140 | − | | 80 | 80 | − | |
| 30 | 160 | − | | 80 | 100 | − | |

TABLE 18

Combination of Busan 1504 with Germall II vs A. niger

| BS1504 (ppm) | Germl II (ppm) | Growth | SI | BS1504 (ppm) | Germl II (ppm) | Growth | SI |
|---|---|---|---|---|---|---|---|
| 300 | 0 | + | | 200 | 250 | + | |
| 400 | 0 | + | | 200 | 500 | + | |
| 500 | 0 | + | | 200 | 1000 | + | |
| 600 | 0 | + | | 200 | 1500 | − | 0.85 |
| 700 | 0 | + | | 200 | 2000 | − | |
| 800 | 0 | − | | 300 | 250 | + | |
| 0 | 500 | + | | 300 | 500 | + | |
| 0 | 1000 | + | | 300 | 1000 | − | 0.77 |
| 0 | 1500 | + | | 300 | 1500 | − | |
| 0 | 2000 | + | | 300 | 2000 | − | |
| 0 | 2500 | − | | 400 | 100 | + | |
| 0 | 3000 | − | | 400 | 250 | + | |
| 10 | 500 | + | | 400 | 500 | + | |
| 10 | 1000 | + | | 400 | 1000 | − | 0.90 |
| 10 | 1500 | + | | 400 | 1500 | − | |
| 10 | 2000 | + | | 400 | 2000 | − | |
| 10 | 2500 | − | | 500 | 100 | + | |
| 50 | 500 | + | | 500 | 250 | + | |
| 50 | 1000 | + | | 500 | 500 | + | |
| 50 | 1500 | + | | 500 | 1000 | − | |
| 50 | 2000 | − | 0.86 | 500 | 1500 | − | |
| 50 | 2500 | − | | 600 | 100 | + | |
| 100 | 500 | + | | 600 | 250 | + | |
| 100 | 1000 | + | | 600 | 500 | − | 0.95 |
| 100 | 1500 | − | 0.73 | 600 | 1000 | − | |
| 100 | 2000 | − | | 600 | 1500 | − | |
| | | | | 700 | 100 | + | |
| | | | | 700 | 250 | + | |
| | | | | 700 | 500 | − | |
| | | | | 700 | 1000 | − | |
| | | | | 700 | 1500 | − | |

TABLE 19

Combination of Busan 1504 and Germall 115 vs P. aeruginosa

| BS1504 (ppm) | G115 (ppm) | Growth | SI | BS1504 (ppm) | G115 (ppm) | Growth | SI |
|---|---|---|---|---|---|---|---|
| 40 | 0 | + | | 30 | 100 | + | |
| 60 | 0 | + | | 30 | 200 | + | |
| 80 | 0 | + | | 30 | 300 | + | |
| 100 | 0 | + | | 30 | 400 | − | |
| 120 | 0 | + | | 30 | 500 | − | |
| 140 | 0 | − | | 30 | 600 | − | |
| 160 | 0 | − | | 40 | 50 | + | |
| 180 | 0 | − | | 40 | 100 | + | |
| 0 | 100 | + | | 40 | 200 | + | |
| 0 | 200 | + | | 40 | 300 | − | 0.88 |
| 0 | 300 | + | | 40 | 400 | − | |
| 0 | 400 | + | | 40 | 500 | − | |
| 0 | 500 | − | | 50 | 50 | + | |
| 0 | 600 | − | | 50 | 100 | + | |
| 10 | 100 | + | | 50 | 200 | + | |
| 10 | 200 | + | | 50 | 300 | − | 0.96 |
| 10 | 300 | + | | 50 | 400 | − | |
| 10 | 400 | + | | 50 | 500 | − | |
| 10 | 500 | − | | 60 | 50 | + | |
| 10 | 600 | − | | 60 | 100 | + | |
| 20 | 100 | + | | 60 | 200 | − | 0.83 |
| 20 | 200 | + | | 60 | 300 | − | |
| 20 | 300 | + | | 60 | 400 | − | |
| 20 | 400 | − | 0.94 | 60 | 500 | − | |
| 20 | 500 | − | | 70 | 20 | + | |
| 20 | 600 | − | | 70 | 50 | + | |
| | | | | 70 | 100 | + | |
| | | | | 70 | 200 | − | 0.90 |
| | | | | 70 | 300 | − | |
| | | | | 80 | 20 | + | |
| | | | | 80 | 50 | + | |
| | | | | 80 | 100 | − | 0.77 |
| | | | | 80 | 200 | − | |
| | | | | 80 | 300 | − | |

TABLE 20

Combination of Busan 1504 with Germall 115 vs A. niger

| BS1504 (ppm) | Germ 115 (ppm) | Growth | SI | BS1504 (ppm) | Germ 115 (ppm) | Growth | SI |
|---|---|---|---|---|---|---|---|
| 300 | 0 | + | | 200 | 1000 | + | |
| 400 | 0 | + | | 200 | 2000 | + | |
| 500 | 0 | + | | 200 | 3000 | + | |
| 600 | 0 | + | | 200 | 4000 | + | |
| 700 | 0 | + | | 200 | 5000 | + | |
| 800 | 0 | − | | 200 | 6000 | + | |
| 0 | 2000 | + | | 200 | 7000 | − | 1.05 |
| 0 | 4000 | + | | 300 | 1000 | + | |
| 0 | 5000 | + | | 300 | 2000 | + | |
| 0 | 6000 | + | | 300 | 3000 | + | |
| 0 | 8000 | − | | 300 | 4000 | + | |
| 0 | 10000 | − | | 300 | 5000 | − | 1.00 |
| 10 | 2000 | + | | 300 | 6000 | − | |
| 10 | 4000 | + | | 400 | 1000 | + | |
| 10 | 5000 | + | | 400 | 2000 | + | |
| 10 | 6000 | + | | 400 | 3000 | + | |
| 10 | 7000 | + | | 400 | 4000 | − | 1.00 |
| 10 | 8000 | + | | 400 | 5000 | − | |
| 50 | 2000 | + | | 400 | 6000 | − | |
| 50 | 4000 | + | | 500 | 1000 | + | 1.03 |
| 50 | 5000 | + | | 500 | 2000 | + | |
| 50 | 6000 | + | | 500 | 3000 | − | 1.00 |
| 50 | 7000 | + | | 500 | 4000 | − | |
| 50 | 8000 | − | 1.06 | 500 | 5000 | − | |
| 100 | 2000 | + | | 500 | 6000 | − | |
| 100 | 4000 | + | | | | | |
| 100 | 5000 | + | | | | | |
| 100 | 6000 | + | | | | | |
| 100 | 7000 | + | | | | | |
| 100 | 8000 | − | 1.12 | | | | |

TABLE 21

Combination of Busan 1504 and Bronopol vs P. aeruginosa

| BS1504 (ppm) | Bronopol (ppm) | Growth | SI | BS1504 (ppm) | Bronopol (ppm) | Growth | SI |
|---|---|---|---|---|---|---|---|
| 40 | 0 | + | | 30 | 0.5 | + | |
| 60 | 0 | + | | 30 | 1 | + | |
| 80 | 0 | + | | 30 | 2 | − | 0.75 |
| 100 | 0 | + | | 30 | 3 | − | |
| 120 | 0 | − | | 30 | 4 | − | |
| 140 | 0 | − | | 30 | 5 | − | |
| 160 | 0 | − | | 40 | 0.5 | + | |
| 180 | 0 | − | | 40 | 1 | + | |
| 0 | 0.5 | + | | 40 | 2 | − | 0.83 |
| 0 | 1 | + | | 40 | 3 | − | |
| 0 | 2 | + | | 40 | 4 | − | |
| 0 | 3 | + | | 40 | 5 | − | |
| 0 | 4 | − | | 50 | 0.2 | + | |

TABLE 21-continued

Combination of Busan 1504 and Bronopol vs *P. aeruginosa*

| BS1504 (ppm) | Bronopol (ppm) | Growth | SI | BS1504 (ppm) | Bronopol (ppm) | Growth | SI |
|---|---|---|---|---|---|---|---|
| 0 | 5 | − | | 50 | 0.5 | + | |
| 0 | 8 | − | | 50 | 1 | + | |
| 0 | 10 | − | | 50 | 2 | − | 0.92 |
| 10 | 0.5 | + | | 50 | 3 | − | |
| 10 | 1 | + | | 50 | 4 | − | |
| 10 | 2 | + | | 60 | 0.2 | + | |
| 10 | 3 | − | 0.83 | 60 | 0.5 | + | |
| 10 | 4 | − | | 60 | 1 | + | |
| 10 | 5 | − | | 60 | 2 | − | |
| 20 | 0.5 | + | | 60 | 3 | − | |
| 20 | 1 | + | | 60 | 4 | − | |
| 20 | 2 | + | | 70 | 0.2 | + | |
| 20 | 3 | − | 0.92 | 70 | 0.5 | + | |
| 20 | 4 | − | | 70 | 1 | − | 0.83 |
| 20 | 5 | − | | 70 | 2 | − | |
| | | | | 70 | 3 | − | |
| | | | | 80 | 0.2 | + | |
| | | | | 80 | 0.5 | + | |
| | | | | 80 | 1 | − | 0.92 |
| | | | | 80 | 2 | − | |
| | | | | 80 | 3 | − | |

TABLE 22

Combination of Busan 1504 with Bronopol vs *A. niger*

| BS1504 (ppm) | Bronopol (ppm) | Growth | SI | BS1504 (ppm) | Bronopol (ppm) | Growth | SI |
|---|---|---|---|---|---|---|---|
| 300 | 0 | + | | 200 | 100 | + | |
| 400 | 0 | + | | 200 | 200 | + | |
| 500 | 0 | + | | 200 | 300 | + | |
| 600 | 0 | + | | 200 | 400 | − | 0.86 |
| 700 | 0 | − | | 200 | 500 | − | |
| 800 | 0 | − | | 200 | 600 | − | |
| 0 | 300 | + | | 200 | 700 | − | |
| 0 | 400 | + | | 300 | 50 | + | |
| 0 | 500 | + | | 300 | 100 | + | |
| 0 | 600 | + | | 300 | 200 | + | |
| 0 | 700 | − | | 300 | 300 | − | 0.86 |
| 0 | 800 | − | | 300 | 400 | − | |
| 0 | 1000 | − | | 300 | 500 | − | |
| 10 | 300 | + | | 300 | 600 | − | |
| 10 | 400 | + | | 300 | 700 | − | |
| 10 | 500 | + | | 400 | 50 | + | |
| 10 | 600 | − | 0.87 | 400 | 100 | + | |
| 10 | 700 | − | | 400 | 200 | − | 0.86 |
| 10 | 800 | − | | 400 | 300 | − | |
| 50 | 300 | + | | 400 | 400 | − | |
| 50 | 400 | + | | 400 | 500 | − | |
| 50 | 500 | + | | 400 | 600 | − | |
| 50 | 600 | − | 0.93 | 500 | 20 | + | |
| 50 | 700 | − | | 500 | 50 | + | |
| 50 | 800 | − | | 500 | 100 | − | 0.86 |
| 100 | 100 | + | | 500 | 200 | − | |
| 100 | 200 | + | | 500 | 300 | − | |
| 100 | 300 | + | | 500 | 400 | − | |
| 100 | 400 | + | | 500 | 500 | − | |
| 100 | 500 | − | 0.86 | 600 | 20 | + | |
| 100 | 600 | − | | 600 | 50 | + | |
| 100 | 700 | − | | 600 | 100 | − | |
| | | | | 600 | 200 | − | |
| | | | | 600 | 300 | − | |
| | | | | 600 | 400 | − | |

TABLE 23

Combination of Busan 1504 with Glydant vs *Ps. aeruginosa*

| BS1504 (ppm) | Glydant (ppm) | Growth | SI | BS1504 (ppm) | Glydant (ppm) | Growth | SI |
|---|---|---|---|---|---|---|---|
| 40 | 0 | + | | 30 | 100 | + | |
| 60 | 0 | + | | 30 | 200 | + | |
| 80 | 0 | + | | 30 | 300 | − | 0.96 |
| 100 | 0 | + | | 30 | 400 | − | |
| 120 | 0 | + | | 30 | 500 | − | |
| 140 | 0 | − | | 30 | 600 | − | |
| 160 | 0 | − | | 40 | 50 | + | |
| 180 | 0 | − | | 40 | 100 | + | |
| 0 | 100 | + | | 40 | 200 | + | |
| 0 | 200 | + | | 40 | 300 | − | |
| 0 | 300 | + | | 40 | 400 | − | |
| 0 | 400 | − | | 40 | 500 | − | |
| 0 | 500 | − | | 50 | 25 | + | |
| 0 | 600 | − | | 50 | 50 | + | |
| 10 | 100 | + | | 50 | 100 | + | |
| 10 | 200 | + | | 50 | 200 | − | 0.86 |
| 10 | 300 | − | 0.82 | 50 | 300 | − | |
| 10 | 400 | − | | 50 | 400 | − | |
| 10 | 500 | − | | 60 | 25 | + | |
| 10 | 600 | − | | 60 | 50 | + | |
| 20 | 100 | + | | 60 | 100 | + | |
| 20 | 200 | + | | 60 | 200 | − | 0.93 |
| 20 | 300 | − | 0.89 | 60 | 300 | − | |
| 20 | 400 | − | | 60 | 400 | − | |
| 20 | 500 | − | | 70 | 10 | + | |
| 20 | 600 | − | | 70 | 25 | + | |
| | | | | 70 | 50 | + | |
| | | | | 70 | 100 | − | |
| | | | | 70 | 200 | − | |
| | | | | 70 | 300 | − | |
| | | | | 80 | 10 | + | |
| | | | | 80 | 25 | + | |
| | | | | 80 | 50 | + | |
| | | | | 80 | 100 | + | |
| | | | | 80 | 200 | + | |
| | | | | 80 | 300 | − | |

TABLE 24

Combination of Busan 1504 with Glydant vs *A. niger*

| BS1504 (ppm) | Glydant (ppm) | Growth | SI | BS1504 (ppm) | Glydant (ppm) | Growth | SI |
|---|---|---|---|---|---|---|---|
| 300 | 0 | + | | 200 | 250 | + | |
| 400 | 0 | + | | 200 | 500 | + | |
| 500 | 0 | + | | 200 | 1000 | − | 0.68 |
| 600 | 0 | + | | 200 | 1500 | − | |
| 700 | 0 | − | | 200 | 2000 | − | |
| 800 | 0 | − | | 300 | 250 | + | |
| 0 | 500 | + | | 300 | 500 | + | |
| 0 | 1000 | + | | 300 | 1000 | − | 0.83 |
| 0 | 1500 | + | | 300 | 1500 | − | |
| 0 | 2000 | + | | 300 | 2000 | − | |
| 0 | 2500 | − | | 400 | 100 | + | |
| 0 | 3000 | − | | 400 | 250 | + | |
| 10 | 500 | + | | 400 | 500 | + | |
| 10 | 1000 | + | | 400 | 1000 | − | 0.97 |
| 10 | 1500 | + | | 400 | 1500 | − | |
| 10 | 2000 | + | | 400 | 2000 | − | |
| 10 | 2500 | − | | 500 | 100 | + | |
| 10 | 3000 | − | | 500 | 250 | + | |
| 50 | 500 | + | | 500 | 500 | − | 0.91 |
| 50 | 1000 | + | | 500 | 1000 | − | |
| 50 | 1500 | + | | 500 | 1500 | − | |
| 50 | 2000 | − | 0.87 | 600 | 50 | + | |
| 50 | 2500 | − | | 600 | 100 | + | |
| 50 | 3000 | − | | 600 | 250 | + | |
| 100 | 500 | + | | 600 | 500 | − | |

TABLE 24-continued

Combination of Busan 1504 with Glydant vs *A. niger*

| BS1504 (ppm) | Glydant (ppm) | Growth | SI | BS1504 (ppm) | Glydant (ppm) | Growth | SI |
|---|---|---|---|---|---|---|---|
| 100 | 1000 | + |  | 600 | 1000 | − |  |
| 100 | 1500 | + |  | 700 | 50 | + |  |
| 100 | 2000 | − | 0.94 | 700 | 100 | + |  |
| 100 | 2500 | − |  | 700 | 250 | − |  |
| 100 | 3000 | − |  | 700 | 500 | − |  |
|  |  |  |  | 700 | 1000 | − |  |

What is claimed is:

1. A composition comprising (a) a compound having the formula (I)

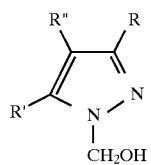

where R and R' are independently selected from hydrogen and alkyl of 1 to 4 carbon atoms, R" is a moiety selected from the group consisting of (a) hydrogen, (b) a halogen atom selected from the group consisting of F, Cl, Br, and I, and (c) a nitro group, or the hydrochloride salt of said compound; and (b) at least one preservative selected from 2-bromo-2-nitro-propane-1,3 diol; dimethylhydantoin; imidazdidinyl urea; diazolidinyl urea; or 1-(3-chloroallyl)-3,5,7-triaza-1-azoniaadamantane chloride; wherein said components (a) and (b) are present in a combined amount synergistically effective to control the growth of a bacterium, fungus, or a mixture thereof.

2. The composition of claim 1, wherein said compound of formula I is 3,5,-dimethyl-1-hydroxymethylpyrazole.

3. The composition of claim 1, wherein said bacterium or fungus is *Aspergillus niger* or *Pseudomonas aeruginosa*.

4. The composition of claim 1, wherein the weight ratio of (a) to (b) is from about 0.1:99 to about 99:0.1.

5. The composition of claim 4, wherein the weight ratio of (a) to (b) is from about 1:30 to about 30:1.

6. The composition of claim 5, where the weight ratio of (a) to (b) is from about 1:5 to about 5:1.

7. The composition of claim 1, wherein said preservative is 2-bromo-2-nitropropane-1,3 diol.

8. The composition of claim 1, wherein said preservative is dimethylhydantoin.

9. The composition of claim 1, wherein said preservative is imidazdidinyl urea.

10. The composition of claim 1, wherein said preservative is diazolidinyl urea.

11. The composition of claim 1, wherein said preservative is 1-(3-chloroallyl)-3,5,7-triaza-1-azoniaadamantane chloride.

12. The composition of claim 1, wherein said composition consists essentially of components (a) and (b).

13. A method of controlling the growth of at least one microorganism selected from a bacterium, fungus, or a mixture thereof, in or on a material or medium susceptible to attack by the microorganism comprising the step of adding to the material or medium a composition comprising (a) a compound having the formula (I)

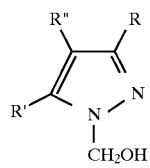

where R and R' are independently selected from hydrogen and alkyl of 1 to 4 carbon atoms, R" is a moiety selected from the group consisting of (a) hydrogen, (b) a halogen atom selected from the group consisting of F, Cl, Br, and I, and (c) a nitro group, or the hydrochloride salt of said compound; and (b) at least one preservative selected from 2-bromo-2-nitropropane-1,3 diol; dimethylhydantoin; imidazdidinyl urea; diazolidinyl urea; or 1-(3-chloroallyl)-3,5,7-triaza-1-azoniaadamantane chloride; wherein said components (a) and (b) are present in a combined synergistically effective amount to control said growth.

14. The method of claim 13, wherein said compound of formula I is 3,5,-dimethyl-1-hydroxymethyl pyrazole.

15. The composition of claim 13, wherein said bacterium or fungus is *Aspergillus niger* or *Pseudomonas aeruginosa*.

16. The method of claim 13, wherein said material or medium is wood pulp, wood chips, wood, lumber, paints, dyes, leathers, adhesives, coatings, animal hides, tanning liquors, paper mill liquors, metal working fluids, starch, petrochemicals, acrylic latex paint emulsions, pharmaceutical formulations, cooling tower water, cosmetics and toiletry formulations, textiles, influent and effluent plant waters, waste water, geological drilling lubricants or agrochemical compositions.

17. The method of claim 14, wherein the material or medium is in the form of a solid, dispersion, emulsion or solution.

18. The method of claim 13, wherein said components (a) and (b) can be added separately to the material or medium.

19. The method of claim 13, wherein said preservative is 2-bromo-2-nitropropane-1,3 diol.

20. The method of claim 13, wherein said preservative is dimethylhydantoin.

21. The method of claim 13, wherein said preservative is imidazdidinyl urea.

22. The method of claim 13, wherein said preservative is diazolidinyl urea.

23. The method of claim 13, wherein said preservative is 1-(3-chloroallyl)-3,5,7-triaza-1-azoniaadamantane chloride.

24. The method of claim 13, wherein said composition consists essentially of components (a) and (b).

25. A method for preventing spoilage of a material or medium caused by bacteria or fungi comprising the step of adding to a material or medium a composition comprising (a) a compound having the formula (I)

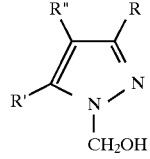

where R and R' are independently selected from hydrogen and alkyl of 1 to 4 carbon atoms, R" is a moiety selected from the group consisting of (a) hydrogen, (b) a halogen atom selected from the group consisting of F, Cl, Br, and I, and (c) a nitro group, or the hydrochloride salt of said compound; and (b) at least one preservative selected from 2-bromo-2-nitropropane-1,3 diol; dimethylhydantoin; imidazdidinyl urea; diazolidinyl urea; or 1-(3-chloroallyl)-3,5,7-triaza-1-azoniaadamantane chloride; wherein said components (a) and (b) are present in a combined synergistically effective amount to prevent or mitigate said spoilage.

26. The method of claim 25, wherein said compound of formula I is 3,5,-dimethyl-1-hydroxymethyl pyrazole.

* * * * *